United States Patent
Haas et al.

[11] Patent Number: 6,096,205
[45] Date of Patent: Aug. 1, 2000

[54] HAND PORTABLE THIN-LAYER CHROMATOGRAPHY SYSTEM

[75] Inventors: Jeffrey S. Haas, San Ramon; Fredrick R. Kelly, Modesto; John F. Bushman, Oakley; Michael H. Wiefel, La Honda; Wayne A. Jensen, Livermore, all of Calif.

[73] Assignee: The Regents of the University of California, Oakland, Calif.

[21] Appl. No.: 09/078,313

[22] Filed: May 13, 1998

[51] Int. Cl.⁷ ........................................... B01D 15/08
[52] U.S. Cl. ................... 210/198.3; 422/70; 422/101; 422/104
[58] Field of Search ............... 210/198.3, 198.2, 210/658; 436/162; 422/61, 70, 101, 104; 294/27.1, 143; 396/565, 587

[56] References Cited

U.S. PATENT DOCUMENTS 5,254,315  10/1993  Nurse et al. .
5,350,510   9/1994  Partney, Jr. ..................... 210/198.3

*Primary Examiner*—W. L. Walker
*Assistant Examiner*—Marianne Ocampo
*Attorney, Agent, or Firm*—Daryl S. Grzybicki

[57] ABSTRACT

A hand portable, field-deployable thin-layer chromatography (TLC) unit and a hand portable, battery-operated unit for development, illumination, and data acquisition of the TLC plates contain many miniaturized features that permit a large number of samples to be processed efficiently. The TLC unit includes a solvent tank, a holder for TLC plates, and a variety of tool chambers for storing TLC plates, solvent, and pipettes. After processing in the TLC unit, a TLC plate is positioned in a collapsible illumination box, where the box and a CCD camera are optically aligned for optimal pixel resolution of the CCD images of the TLC plate. The TLC system includes an improved development chamber for chemical development of TLC plates that prevents solvent overflow.

14 Claims, 5 Drawing Sheets

HAND PORTABLE THIN-LAYER CHROMATOGRAPHY SYSTEM

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to a hand portable system for performing quantitative thin-layer chromatography analysis.

2. Description of Related Art

Various analytical techniques are used to measure the type and amount of contamination from unknown chemicals in environmental, industrial, civilian, and military situations. Conventional thin-layer chromatography (TLC) analysis is routinely used in analytical laboratories worldwide for quantitative and qualitative characterization of unknowns. This technique is ideal for rapid pre-screening and identification of known and unknown chemicals. TLC allows multiple samples and standards (in mg to ng quantities) to be chromatographed simultaneously on a TLC plate in a solvent tank. Semiquantitative and qualitative assessment from all samples is then readily obtained by inspection of the plates, which may be chemically developed and then illuminated to display the separated components (appearing as spots). Further quantitative analysis may be performed using an illumination box, camera, and data acquisition equipment.

Unfortunately, conventional TLC apparatus is cumbersome, typically made of glass, and is not field-deployable or field-ruggedized for on-site analysis. Current TLC hardware is not hand portable when including all the necessary support equipment such as plates, tanks, solvent, pipettes, ruler, etc. Furthermore, the illumination and data acquisition equipment needed to fully analyze samples is oversized and extremely heavy. Thus, there is a need for a hand portable, field-ready TLC system, including data acquisition capability, that is cost-effective and efficient for analyzing multiple samples of unknown chemicals on-site in a variety of emergency and non-emergency situations.

SUMMARY OF THE INVENTION

The present invention is a hand portable, field-deployable thin-layer chromatography (TLC) system. This system contains many miniaturized features that permit a large number of samples to be processed efficiently. The TLC unit contains a solvent tank, a holder basket for TLC plates, and a variety of chambers for storing TLC tools. The small tank reservoir eliminates the need for a saturation pad, and a mere 10 mL of solvent can process over 100 samples. The holder basket accommodates a convenient number of TLC plates (e.g., six) and is designed to prevent aberrant wicking along the TLC plate edges. Tool chambers are available for storing pipettes, TLC plates, and a container of solvent. The unit has a window for monitoring the solvent level during the TLC plate processing, a swing-out foot for additional stability, and a gasket-sealed, screw-down lid for better solvent equilibration. The unit also includes a stencil that fits over the corner of any standard TLC plate for rapid, accurate marking of TLC plates.

In addition, a hand portable, battery-operated (or AC powered) unit for development, illumination, and data acquisition of the TLC plates has been designed. A TLC plate is positioned in a collapsible illumination box with a CCD camera, where the box and camera are optically aligned for optimal resolution of the CCD images of the TLC plate. An improved, hand portable development chamber for chemical development of TLC plates has also been designed that prevents solvent overflow.

This TLC unit and data acquisition system are ideal for on-site field analysis and identification of unknown chemicals, and there are worldwide applications to forensics, hazardous materials and environmental monitoring, law enforcement, and international treaty verification. Other objects and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

Figure 1:
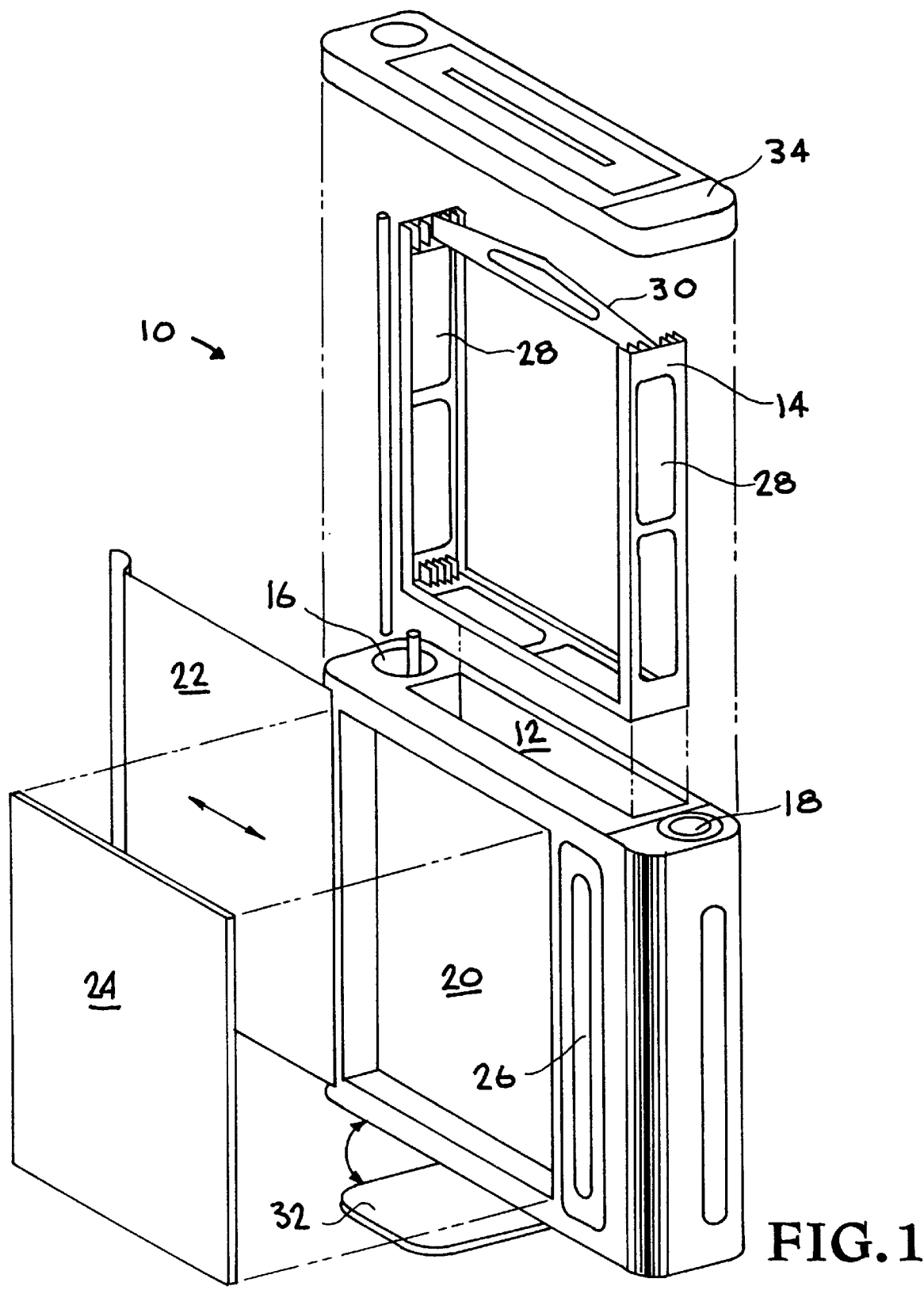
FIG. 1 shows schematically the thin-layer chromatography unit according to the present invention.

The present invention is a hand portable thin-layer chromatography (TLC) system that is field-deployable for on-site analysis. The TLC unit 10 is shown in FIG. 1 and contains a solvent tank 12, a holder basket 14 for TLC plates, and a variety of chambers 16,18,20 in the frame for storing TLC tools (e.g., pipettes, solvent, TLC plates, ruler). The unit may be made of a variety of materials, including stainless steel. The unit can be made quite compact, and is only limited by the size of the TLC plates, which are typically 10 cm×10 cm. For example, the dimensions of a portable, field-deployable unit can be about 6 cm×16 cm×16 cm.

The small tank reservoir 12 eliminates the need for a saturation pad. A mere 10 mL of solvent can be used to process over 100 samples. The solvent can be stored in a container which fits into one of the storage chambers 18. Pipettes can be stored in another chamber 16. A tool chamber 20 at the front of the unit holds extra TLC plates; in one embodiment, a sliding door 22 that clips in place provides access to the TLC plates 24. The TLC unit has a window 26 for visually monitoring the solvent level during the TLC plate processing.

The holder basket 14 fits into the solvent tank 12, and the basket 14 accommodates a convenient number of TLC plates (e.g., six) for processing. The basket 14 has a unitary body comprising two parallel sides and a bottom portion, is designed to prevent aberrant wicking along the TLC plate edges, which causes the separated components of the multiple samples on the TLC plate to be unevenly distributed across the top of the plate. To prevent this effect, the sides (and bottom) of the basket 14 have openings 28 so that the TLC plates do not touch the sides during processing in the solvent. This design provides superior chromatographic separation of the components. Grooves or separators at the top and bottom of the basket 14 prevent the TLC plates from touching one another. The basket 14 has a handle 30 to facilitate the transfer of the basket 14 in and out of the solvent tank 12.

Figure 2:
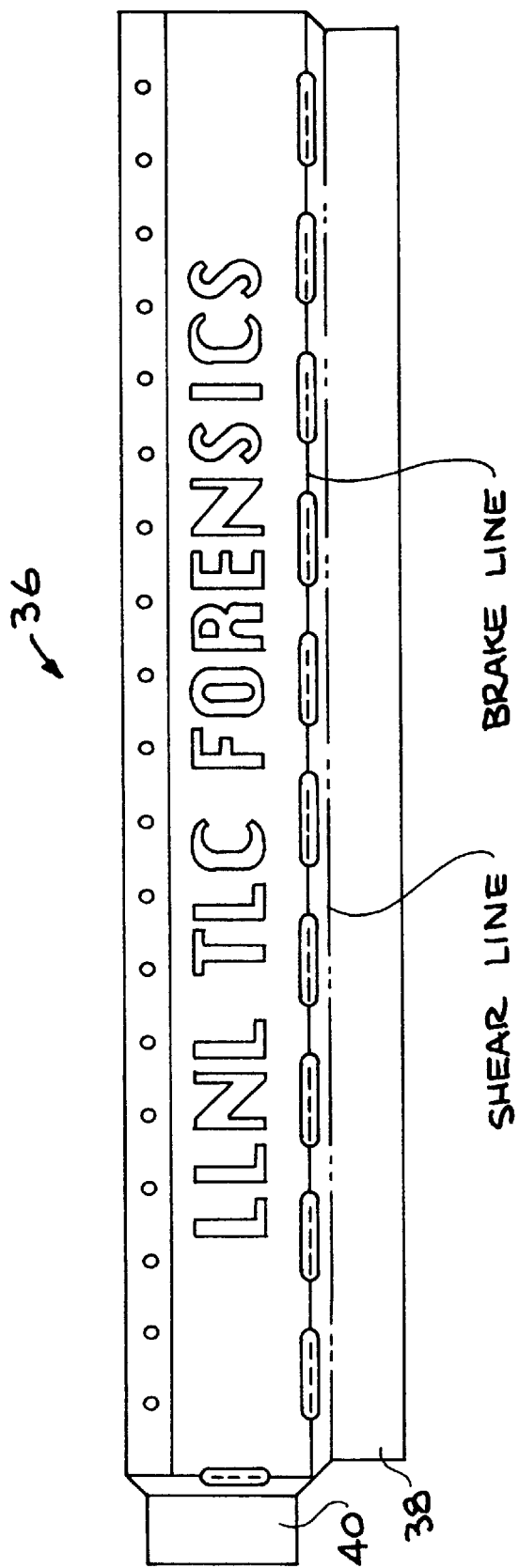
FIG. 2 shows a stencil for marking TLC plates.

The TLC unit also features a foot (or feet) 32 that swings out from the bottom of the unit to provide additional stability. A lid 34 for covering the unit is gasket-sealed and can be screwed down for better solvent equilibration. The TLC unit also includes a straight-edge stencil 36, shown in FIG. 2, having rims 38,40 that fit over the corner of a standard TLC plate for rapid, accurate marking of TLC plates. The stencil 36 fits into the TLC unit, such as in a groove in the lid or in a tool chamber, such as the TLC plate holder 20.

Illumination and Data Acquisition

Figure 3:
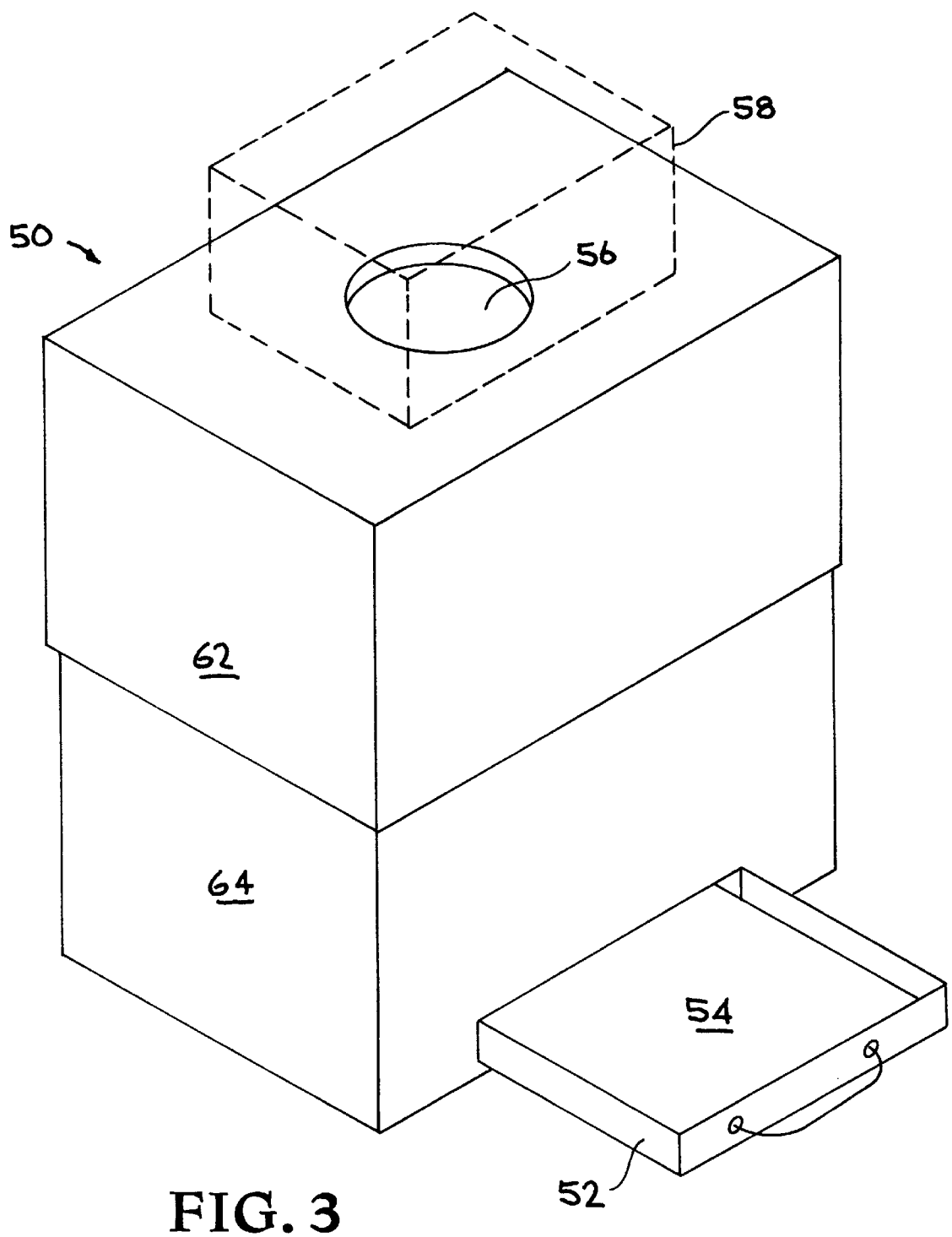
FIG. 3 shows schematically the illumination box according to the present invention.
Figure 4:
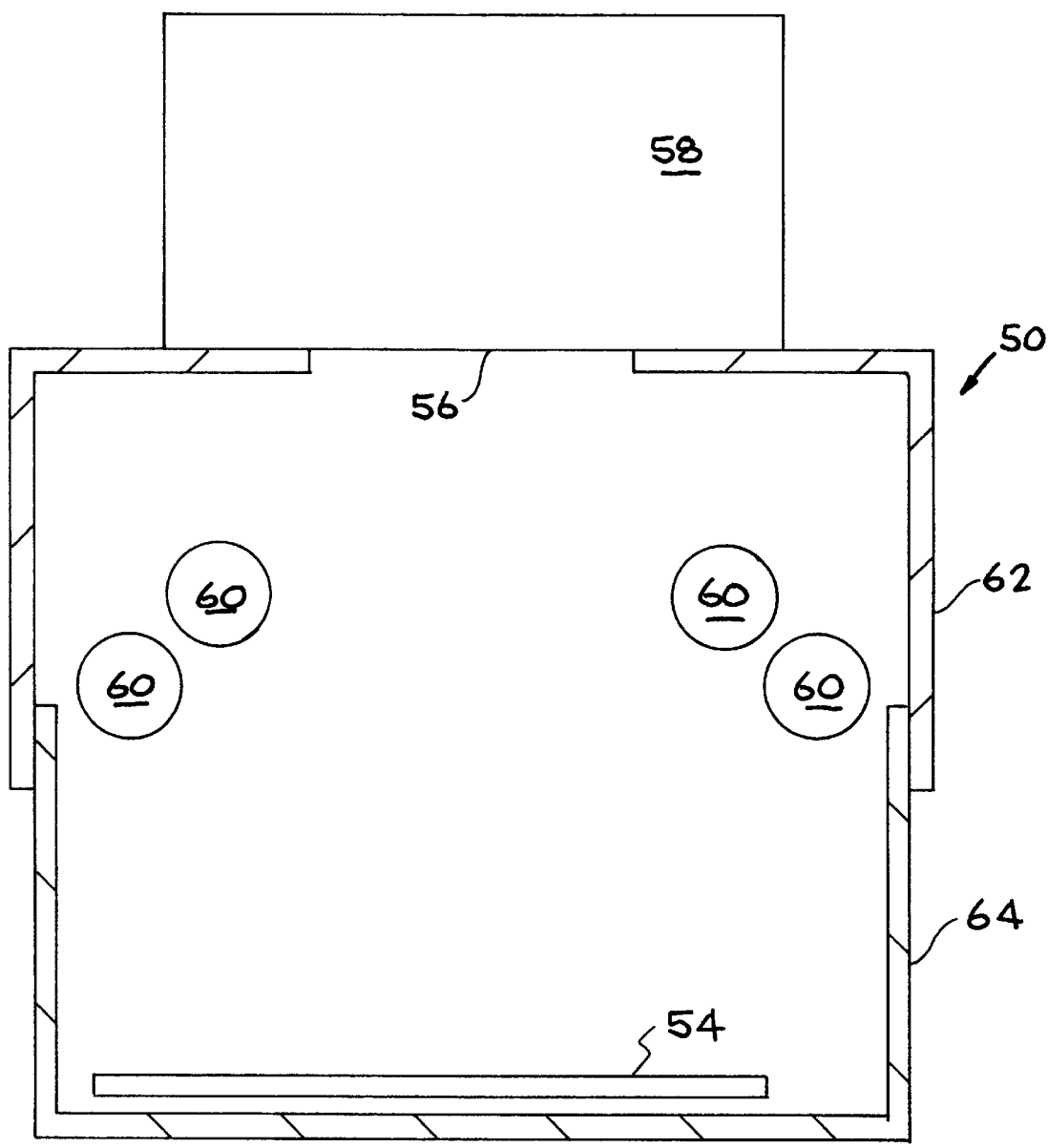
FIG. 4 shows the interior of the illumination box according to the present invention.

A hand portable, battery-operated unit for development, illumination, and data acquisition of the processed TLC plates is shown in FIGS. 3 and 4. After chromatographic separation is complete, extracting quantitative information from the TLC plate requires integration of spot intensity. The separated components may be read directly as spots that fluoresce or may be developed under visible or UV light. FIG. 3 shows the exterior of the illumination box 50, which can be used to develop and illuminate the TLC plates for acquiring CCD camera images. The CCD camera captures very low spot intensities with three-color channels.

In the illustrated embodiment, the TLC plate 54 is introduced into the box 50 through a bottom drawer 52, which slides in and out of the box 50. The box 50 has an aperture 56 directly above the TLC plate, where the lens of a CCD camera 58 is positioned. The box 50 and camera 58 are optically aligned for optimum pixel resolution of the CCD images of a standard TLC plate (10 cm×10 cm). The camera may be a commercially available CCD camera (0.25 in CCD, 640×480 pixels) with 24-bit color resolution, where the data are directly recorded onto a 3.5" floppy disk and can be downloaded directly to a computer. Commercially available software may be used to integrate the intensity of each spot, and then analyze the sample by comparison to known compounds.

The illumination box 50 contains sources of light, preferably for different wavelength regions (e.g., visible, ultraviolet). The embodiment illustrated in FIG. 4 shows four bulbs 60 positioned on two sides of the aperture (two used for visible light, two for UV). Either pair can be switched on to uniformly and optimally illuminate the TLC plate 54 underneath. The light sources can be connected to a battery or, optionally, are AC powered.

The illumination box 50 has a top section 62 and bottom section 64, whereby the top section 62 can be collapsed over the bottom section 64 to further reduce the volume of the box 50 when not in use. The fully expanded box 50 can be made quite compact; for example, the box illustrated in FIG. 3 has dimensions of about 16 cm×12 cm×14 cm. The illumination box may be made from a variety of materials, including stainless steel and plastic.

Figure 6:
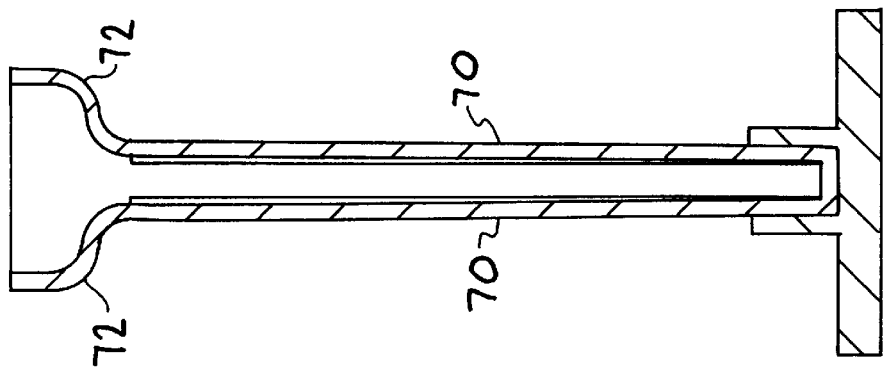
FIG. 6 shows a side view of the TLC development chamber.
Figure 5:
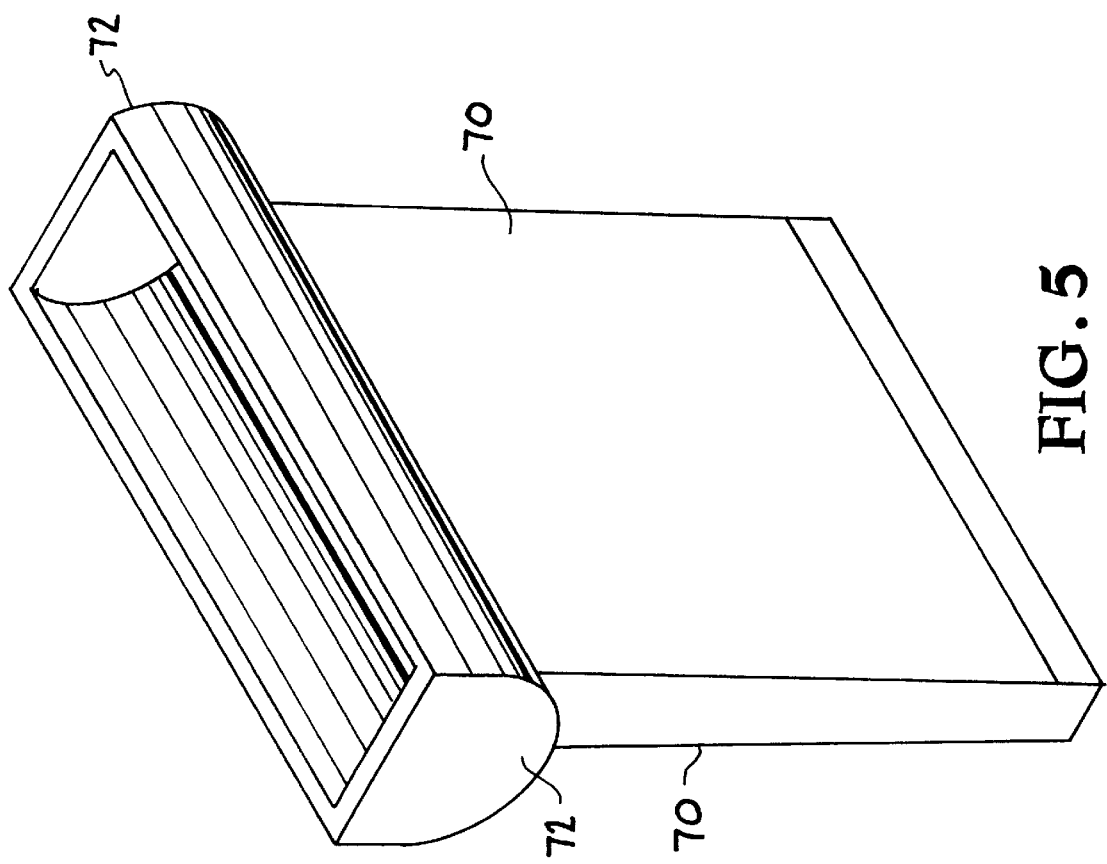
FIG. 5 shows a hand portable TLC development chamber.

FIGS. 5 and 6 shows an improved, hand-held, field-ruggedized development chamber for chemical development of TLC plates that is designed to prevent solvent overflow. The chamber is used to develop the separated components to different colors, which are then viewed in the illumination box. The walls 70 of the chamber taper outward from bottom to top, and the topmost portion of the chamber has curved walls 72 having a bowl-like shape. When the TLC plate is submerged in the development chamber, displaced solvent collects in the expanded, bowl-shaped well region, avoiding overflow problems. A cover for the chamber has been designed to fit directly over the wide mouth of the chamber, and a stand 74 holds the chamber upright. The chamber can be made from various materials, including stainless steel or a lightweight plastic.

The foregoing description of preferred embodiments of the invention is presented for purposes of illustration and description and is not intended to be exhaustive or to limit the invention to the precise form disclosed. Many modifications and variations are possible in light of the above teaching.

What is claimed is:

1. A hand portable thin-layer chromatography system, comprising:

a portable housing unit containing a solvent tank for performing thin-layer chromatography, and a plurality of chambers for storing tools for performing thin-layer chromatography;

a removable holder basket that fits into the solvent tank for holding a plurality of thin-layer chromatography plates said basket having a unitary body comprising two parallel sides and a bottom portion, wherein at least one side of the holder basket has an opening that allows fluid flow into the holder basket; and a top cover for the housing unit.

2. The system as recited in claim 1, further comprising a stencil for marking thin-layer chromatography plates, wherein the stencil fits into a chamber for storing tools in the housing unit.

3. The system as recited in claim 2, wherein the stencil includes a straight edge and a right angle with edges that fit over a corner of a chromatography plate.

4. The system as recited in claim 1, wherein at least one of the tool chambers is designed to hold a plurality of thin-layer chromatography plates.

5. The system as recited in claim 1, wherein at least one of the tool chambers is designed to hold a plurality of pipettes for thin-layer chromatography.

6. The system as recited in claim 1, wherein at least one of the tool chambers is designed to hold a container for a thin-layer chromatography solvent.

7. The system as recited in claim 1, wherein the housing unit contains a window for visually monitoring solvent level in the solvent tank.

8. The system as recited in claim 1, further comprising at least one movable foot plate on the bottom of the housing unit to stabilize the housing unit.

9. The system as recited in claim 1, wherein the sides of the holder basket have openings such that the sides of the chromatography plates do not touch the sides of the holder basket.

10. The system as recited in claim 1, wherein the bottom of the holder basket has an opening that allows fluid flow into the holder basket.

11. The system as recited in claim 1, wherein the housing contains a slidable door to remove chromatography plates from one of the tool chambers.

12. The system as recited in claim 1, wherein the housing unit has dimensions less than about 6 cm×16 cm×16 cm.

13. The system as recited in claim 1, wherein the top cover is a gasket-sealed, screw-down cover.

14. The system as recited in claim 1, wherein the holder basket has a plurality of separators at the bottom of the basket holder to prevent the chromatography plates from touching each other.

* * * * *